United States Patent [19]

Razdan et al.

[11] 4,051,152
[45] Sept. 27, 1977

[54] OXO C-RING BENZOPYRANS

[75] Inventors: Raj Kumar Razdan, Belmont; Haldean Cloyce Dalzell, Weston, both of Mass.; Patricia Herlihy, Dover, N.H.

[73] Assignee: Sharps Associates, Cambridge, Mass.

[21] Appl. No.: 647,050

[22] Filed: Jan. 7, 1976

[51] Int. Cl.² .................. C07D 307/83; C07D 311/80
[52] U.S. Cl. .................... 260/345.3; 424/283
[58] Field of Search ...................... 260/345.3

[56] References Cited

U.S. PATENT DOCUMENTS

| | | | |
|---|---|---|---|
| 3,901,926 | 8/1975 | Winn et al. | 260/345.3 |
| 3,928,598 | 12/1975 | Archer | 260/345.3 |
| 3,941,782 | 3/1976 | Harris et al. | 260/345.3 |

FOREIGN PATENT DOCUMENTS

| | | | |
|---|---|---|---|
| 2,451,932 | 7/1975 | Germany | 260/345.3 |
| 2,451,934 | 7/1975 | Germany | 260/345.3 |

OTHER PUBLICATIONS

Fiechtl et al., Tetrahedron, 31, 479 (1975).

*Primary Examiner*—Bernard Helfin
*Assistant Examiner*—Nicky Chan

*Attorney, Agent, or Firm*—Merriam, Marshall, Shapiro & Klose

[57] ABSTRACT

Benzopyrans of the formula

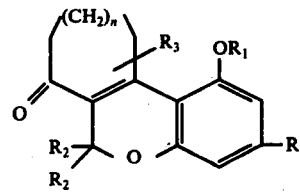

wherein $n$ represents 0 or 1, R is an alkyl group having 1 to 20 carbon atoms, an aryl-lower alkyl group or a cycloalkyl-lower alkyl group, $R_1$ is hydrogen or

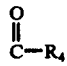

wherein $R_4$ is lower alkyl, phenyl, cycloalkyl-lower alkyl or aryl-lower alkyl, $R_2$ is a lower alkyl and $R_3$ is hydrogen or one or two lower alkyl groups, pharmaceutical compositions containing the compounds, and uses of the compounds as tranquilizers and analgesics.

15 Claims, No Drawings

OXO C-RING BENZOPYRANS

This invention relates to novel chemical compounds and processes of producing the same. More particularly, this invention is concerned with novel benzopyrans and the use of such compounds, particularly those having pharmacological activity.

According to one aspect of the subject invention there is provided novel benzopyran derivatives of the formula

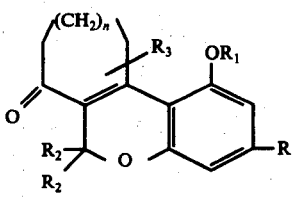

wherein n represents 0 or 1, R represents an alkyl group having 1 to 20 carbon atoms, an aryl-lower alkyl group or a cycloalkyl-lower alkyl group, $R_1$ represents hydrogen or

wherein $R_4$ is lower alkyl, phenyl, cycloalkyl-lower alkyl or aryl-lower alkyl and particularly phenyl-lower alkyl, $R_2$ represents lower alkyl and $R_3$ is hydrogen or one or two lower alkyl groups.

As used herein, the term "lower-alkyl" means saturated, monovalent aliphatic radicals, including straight and branched-chain radicals of from one to six carbon atoms, as illustrated by, but not limited to methyl, ethyl, propyl, isopropyl, butyl, sec.-butyl, amyl, hexyl, and the like.

As used herein, the term "alkyl" means saturated, monovalent aliphatic radicals, including straight and branched-chain radicals of from one to 20 carbon atoms, as illustrated by, but not limited to methyl, n-amyl, n-hexyl, 2-heptyl, n-heptyl, 1,2-dimethylheptyl, n-octyl, 2-nonyl, 2-tetradecyl, n-hexadecyl, 2-eicosanyl, and the like.

As used herein, the term "cycloalkyl" means cyclic, saturated aliphatic radicals having from three to eight carbon atoms, as illustrated by, but not limited to cyclopropyl, cyclobutyl, 2-methylcyclobutyl, cyclohexyl, 4-methylcyclohexyl, cyclooctyl, and the like.

The term arylalkyl means groups having an aryl group joined to an alkyl, and particularly a lower alkyl, group. The aryl group can have a single ring, such as the phenyl group, or a plurality of fully unsaturated rings which can be bonded together or which can be fused rings such as the napthyl group. In addition, the aryl group can be nuclear substituted with one or more halo groups, such as the chloro and fluoro groups, lower alkyl groups such as methyl and ethyl and lower alkoxy groups such as methoxy and ethoxy.

As used herein, the term "lower-alkanoyl" means saturated, monovalent, aliphatic radicals derived from a monocarboxylic acid, including straight or branched-chain radicals of from one to six carbon atoms, as illustrated by, but not limited to formyl, acetyl, propionyl, α-methylpropionyl, butyryl, hexanoyl, and the like.

As used herein, the term "phenyl-lower alkyl," means a monovalent radical consisting of a phenyl nucleus bonded to the rest of the molecule, respectively, through a divalent lower-alkylene radical of from one to four carbon atoms as illustrated by, but not limited to methylene, 1,1-ethylene, 1,2-ethylene, 1,3-propylene, 1,2-propylene and 1,4-butylene. Here and elsewhere throughout this specification, it will be understood the benzene or phenyl ring can bear any number and kind of substituents such as would occur to the man skilled in organic chemistry. Solely for illustration, and without limitation, such substituents include lower-alkyl, lower-alkoxy, halo (chloro, bromo, iodo or fluoro), lower-alkylmercapto, and the like.

More specifically, the compounds provided by this invention and included within the scope of formula I above, may be represented by the following formulas II and III:

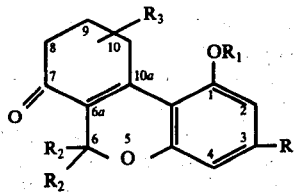

generically named 7,8,9,10-tetrahydro-6H-dibenzo[b,d]-pyrans, and

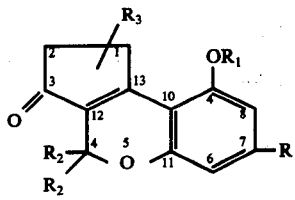

generically named 1,2,3,4-tetrahydrocyclopenta[c] [1] benzopyrans, wherein in each of formulas II and III the R, $R_1$, $R_2$ and $R_3$ have the same meaning as in formula I.

The compounds of formulas II and III of particular interest for pharmacological activity are those in which R is an alkyl having 5 to 9 carbon atoms in the chain, $R_1$ is hydrogen or lower alkanoyl, $R_2$ is methyl and $R_3$ is hydrogen, methyl or dimethyl.

The phenolic starting materials used in producing the compounds of this invention may be represented by formula IV:

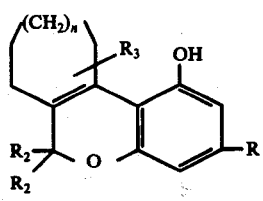

wherein n, R, $R_2$ and $R_3$ have the previously assigned meaning. These starting materials are disclosed in the copending, but now allowed, U.S. patent application of Harris et al. Ser. No. 361,897 filed May 21, 1973 now U.S. Pat. No. 3,941,782 granted Mar. 2, 1976, incorporated herein by reference. Benzopyrans which can be used as starting materials are also disclosed by Adams et al. in J. Am. Chem. Soc., 62, 2245 and 2407 (1940); Adams et al., J. Am. Chem. Soc., 67, 1534 (1945), Mechoulam et al., J. Am. Chem. Soc., 89, 4552 (1967); Bergel et al., J. Chem. Soc., 286 (1943); Avison et al., J. Chem. Soc., 952 (1949); Ghosh et al., J. Chem. Soc., 1118 (1940); Aaron et al., J. of Organic Chem., 33, 684 (1968); Taylor et al., Tetrahedron, 23, 77 (1967); Loev et al., J. Med. Chem., 16, 1200 (1973) and U.S. Pat. Nos. 2,419,935; 2,509,386; 3,388,136; 3,639,426; 3,728,360; 3,886,184 and 3,901,926. Other benzopyran starting materials which may not be specifically disclosed in the prior art can be readily produced according to known procedures by reacting a 5-R-resorcinol, in which R has the previously assigned significance, with a 2-carboloweralkoxy cyclopentanone or cyclohexanone, followed by a Grignard reaction. Many of these compounds are disclosed in Organic Reactions, Volume 15, John Wiley & Sons, Inc. 1967, as see for example pages 51, 52, 61 and 62.

In producing the compounds of this invention the phenolic benzopyrans of formula IV are first esterified to protect the hydroxy group and to deactivate and prevent oxidation of the aromatic ring, the resulting esters (V) are then oxidized to introduce the oxo group and then, if desired, the oxo-ester (VI) compounds are hydrolyzed to obtain the oxo-hydroxy benzopyrans (VII). This process may be represented as follows:

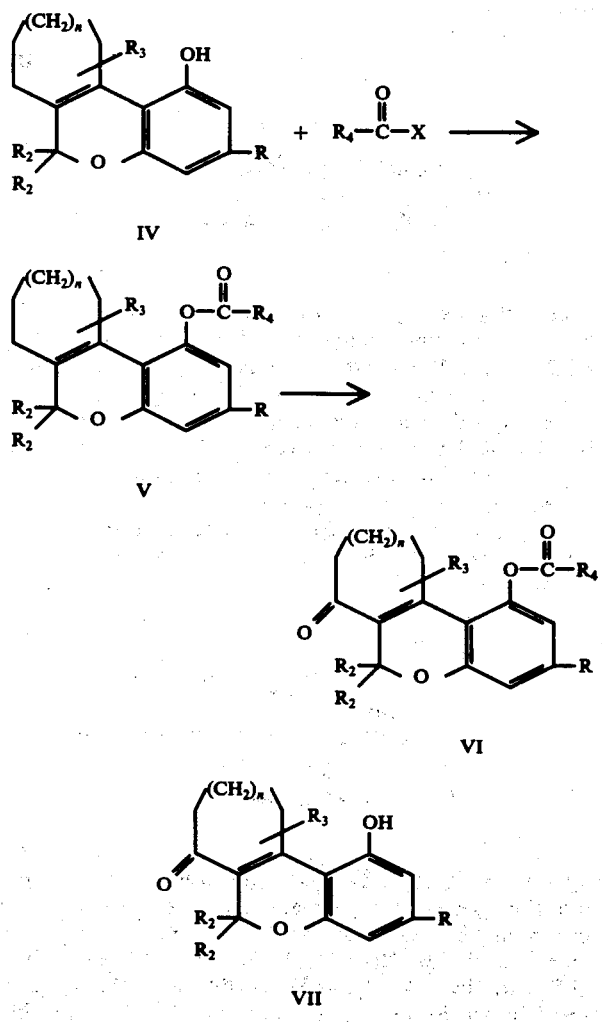

wherein n, R, $R_2$, $R_3$ and $R_4$ have the previously assigned significance and X represents —OH or a reactive halo group such as a chloro or bromo group.

Some of the benzopyrans which can be used as starting materials are: 4,4-dimethyl-7-(1,2-dimethylheptyl)-9-hydroxy-1,2,3,4-tetrahydrocyclopenta[c][1]benzopyran, 7-(1,2-dimethylheptyl)-4,4-diethyl-9-hydroxyl-1,2,3,4-tetrahydrocyclopenta[c][1]benzopyran, 4,4-dimethyl-9-hydroxy-7-(4-phenyl-1-butyl)-1,2,3,4-tetrahydrocyclopenta[c][1]benzopyran, 4,4-diethyl-9-hydroxy-7-octadecyl-1,2,3,4-tetrahydrocyclopenta[c][1]benzopyran, 1-hydroxy-3-pentyl-7,8,9,10-tetrahydro-6,6,9-trimethyl-6H-dibenzo-[b,d]pyran, 3-(3-cyclopentyl-1-propyl)-1-hydroxy-7,8,9,10-tetrahydro-6,6,9-trimethyl-6H-dibenzo[b,d]pyran, 6,6-dimethyl-3-(1,2-dimethylheptyl)-1-hydroxy-7,8,9,10-tetrahydro-6H-dibenzo([b,d]pyran, 6,6-dimethyl-1-hydroxy-3-pentyl-7,8,9,10-tetrahydro-6H-dibenzo[b,d]pyran, 7-(1,2-dimethylheptyl)-9-hydroxy-1,4,4-trimethyl-1,2,3,4-tetrahydrocyclopenta[c][1]benzopyran, 7-(1,2-dimethylheptyl)-9-hydroxy-2,4,4-trimethyl-1,2,3,4-tetrahydrocyclopenta[c][1]benzopyran, 7-(1,2-dimethylheptyl)-9-hydroxy-2,2,4,4-tetramethyl-1,2,3,4-tetrahydrocyclopenta[c][1]benzopyran, 4,4-dimethyl-1-ethyl-9-hydroxy-7-(5-pentyl)-1,2,3,4-tetrahydrocyclopenta[c][1]benzopyran and 3-(1,2-dimethylheptyl)-1-hydroxy-7,8,9,10-tetrahydro-6,6,10-trimethyl-6H-dibenzo[b,d]pyran.

Some of the acids and acyl halides which can be used to produce the esters of the phenolic benzopyrans are lower alkanoic acids, cycloalkyl-lower alkanoic acids, phenyl-lower alkanoic acids and benzoic acid including, for example, acetic acid, propionic acid, benzoic acid, phenylacetic acid, phenylbutyric acid, cyclopentylacetic acid and cyclohexylpropionic acid and the chloro and bromo acyl halides of such acids. The anhydrides of the acids may be used, if desirable, in place of the acids.

The esterification reaction is readily effected under liquid reaction conditions using, for example, an organic solvent which is inert under the conditions of the reaction, such as benzene, toluene, xylene and the like, and in the presence of basic catalyst as, for example, pyridine, triethylamine or dimethylaniline. Anhydrous conditions are preferably used. A moderately elevated temperature up to reflux temperature is usually sufficient to induce reaction and bring it to completion rapidly. After the reaction is terminated the desired product can be isolated from the reaction mixture by conventional procedures.

Some of the benzopyran esters of formula V which are produced as described are: 9-acetoxy-4,4-dimethyl-7-(1,2-dimethylheptyl)-1,2,3,4-tetrahydrocyclopenta[c][1]benzopyran, 4,4-diethyl-9-(3-phenylpropionyloxy)-7-(1,2-dimethylheptyl)-1,2,3,4-tetrahydrocyclopenta[c][1]benzopyran, 9-cyclopentylacetoxy-4,4-dimethyl-7-(4-phenyl-1-butyl)-1,2,3,4-tetrahydrocyclopenta[c][1]benzopyran, 9-benzoyloxy-4,4-diethyl-7-octadecyl-1,2,3,4-tetrahydrocyclopenta[c][1]benzopyran, 1-acetoxy-3-pentyl-7,8,9,10-tetrahydro-6,6,9-trimethyl-6H-dibenzo-[b,d]pyran, 1-benzoyloxy-3-(3-cyclopentyl-1-propyl)-7,8,9,10-tetrahydro-6,6,9-trimethyl-6H-dibenzo [b,d]pyran, 1-cyclopentylacetoxy-6,6-dimethyl-3-(1,2-dimethylheptyl)-7,8,9,10-tetrahydro-6H-dibenzo b,d]-pyran, 1-(3-cyclohexylpropionyloxy)-6,6-dimethyl-3-pentyl-7,8,9,10-tetrahydro-6H-dibenzo[b,d]pyran, 7-(1,2-dimethylheptyl)-9-propionyloxy-1,4,4-trimethyl-1,2,3,4-tetrahydrocyclopenta[c][1]benzopyran, 9-acetoxy-7-(1,2-dimethylheptyl)-2,4,4-trimethyl-1,2,3,4- tetrahydrocyclopentac][1]benzopyran, 9-acetoxy-7-(5-pentyl)-2,2,4,4-tetramethyl-1,2,3,4-tetrahydrocyclopenta[c][1]benzopyran, 4,4-dimethyl-7-(1,2-dimethylheptyl)-1-ethyl-9-(4-phenylbutyryloxy)-1,2,3,4-tetrahydrocyclopenta[c][1]benzopyran and 1-acetoxy-3-(1,2-dimethylheptyl)-7,8,9,10-tetrahydro-6,6,10-trimethyl-6H-dibenzo[b,d]pyran.

The oxo-ester benzopyrans of formula VI are readily produced by reacting the esters of formula V with an oxidizing agent. The oxo group is readily introduced into the c-ring of the benzopyran compounds by ceric ammonium nitrate in aqueous acidic solution. Some representative aqueous acidic solutions which can be used are 6M perchloric acid, 3.5–6M nitric acid, 50–100% acetic acid and 45% formic acid. A moderately elevated temperature of up to 80°–100° C. is generally suitable for the reaction, which is usually completed in 1 to 2 hours. Following termination of the reaction, the desired oxo-ester can be recovered from the reaction mixture by conventional methods, such as extraction with ethyl ether.

Some of the oxo-ester benzopyrans of formula VI which are produced as described are: 9-acetoxy-4,4-dimethyl-7-(1,2-dimethylheptyl)-3-oxo-1,2,3,4-tetrahydrocyclopenta[c][1]benzopyran, 4,4-diethyl-7-(1,2-dimethylheptyl)-3-oxo-9-(3-phenylpropionyloxy)-1,2,3,4-tetrahydrocyclopenta[c][1]benzopyran, 9-cyclopentylacetoxy-4,4-dimethyl-3-oxo-7-(4-phenyl-1-butyl)-1,2,3,4-tetrahydrocyclopenta[c][1]benzopyran, 9-benzoyloxy-4,4-diethyl-7-octadecyl-3-oxo-1,2,3,4-tetrahydrocyclopenta[c][1]benzopyran, 1-acetoxy-7-oxo-3-pentyl-7,8,9,10-tetrahydro-6,6,9-trimethyl-6H-dibenzo[b,d]pyran, 1-benzoyloxy-3-(3-cyclopentyl-1-propyl)-7-oxo-7,8,9,10-tetrahydro-6,6,9-trimethyl-6H-dibenzo[b,d]pyran, 1-cyclopentylacetoxy-6,6-dimethyl-3-(1,2-dimethylheptyl)-7-oxo-7,8,9,10-tetrahydro-6H-dibenzo[b,d]pyran, 1-(3-cyclohexylpropionyloxy)-6,6-dimethyl-7-oxo-3-pentyl-7,8,9,10-tetrahydro-6H-dibenzo[b,d]pyran, 7-(1,2-dimethylheptyl)-9-propionyloxy-3-oxo-1,4,4-trimethyl-1,2,3,4-tetrahydrocyclopenta[c][1]benzopyran, 9-acetoxy-7-(1,2-dimethylheptyl)-3-oxo-2,4,4-trimethyl-1,2,3,4-tetrahydrocyclopenta[c][1]benzopyran, 9-acetoxy-7-(5-pentyl)-3-oxo-2,2,4,4-tetramethyl-1,2,3,4-tetrahydrocyclopenta[c][1]benzopyran, 4,4-dimethyl-7-(1,2-dimethylheptyl)-1-ethyl-3-oxo-9-(4-phenylbutyryloxy)-1,2,3,4-tetrahydrocyclopenta[c][1]benzopyran and 1-acetoxy-3-(1,2-dimethylheptyl)-7-oxo-7,8,9,10-tetrahydro-6,6,10-trimethyl-6H-dibenzo[b,d]pyran.

The oxo-ester benzopyran compounds of formula VI are readily hydrolyzed by use of an aqueous base, such as sodium hydroxide or potassium hydroxide, to cleave the ester group and form the oxo-hydroxy benzopyrans of formula VII. After the hydrolysis is terminated the reaction mixture may be acidified and then extracted with diethyl ether to remove the desired oxo-hydroxy compound from the mixture. The product may then be isolated by conventional means.

Some of the oxo-hydroxy benzopyrans of formula VII which are produced as described are: 4,4-dimethyl-7-(1,2-dimethylheptyl)-9-hydroxy-3-oxo-1,2,3,4-tetrahydrocyclopenta[c][1]benzopyran, 4,4-diethyl-7-(1,2-dimethylheptyl)-9-hydroxy-3-oxo-1,2,3,4-tetrahydrocyclopenta[c][1]benzopyran, 4,4-dimethyl-9-hydroxy-3-oxo-7-(4-phenyl-1-butyl)-1,2,3,4-tetrahydrocyclopenta[c][1]benzopyran, 4,4-diethyl-9-hydroxy-7-octadecyl-3-oxo-1,2,3,4-tetrahydrocyclopenta[c][1]benzopyran, 1-hydroxy-7-oxo-3-pentyl-7,8,9,10-tetrahydro-6,6,9-trimethyl-6H-dibenzo[b,d]pyran, 3-(3-cyclopentyl-1-propyl)-1-hydroxy-7-oxo-7,8,9,10-tetrahydro-6,6,9-trimethyl-6H-dibenzo[b,d]pyran, 6,6-dimethyl-3-(1,2-dimethylheptyl)-1-hydroxy-7-oxo-7,8,9,10-tetrahydro-6H-dibenzo[b,d]pyran, 6,6-dimethyl-1-hydroxy-7-oxo-3-pentyl-7,8,9,10-tetrahydro-6H-dibenzo[b,d]pyran, 7-(1,2-dimethylheptyl)-9-hydroxy-3-oxo-1,4,4,-trimethyl-1,2,3,4-tetrahydrocyclopenta[c][1]benzopyran, 7-(1,2-dimethylheptyl)-9-hydroxy-3-oxo-2,4,4-trimethyl-1,2,3,4-tetrahydrocyclopenta[c][1]benzopyran, 9-hydroxy-7-(5-pentyl)-3-oxo-2,2,4,4-tetramethyl-1,2,3,4-tetrahydrocyclopenta[c][1]benzopyran, 4,4-dimethyl-7-(1,2-dimethylheptyl)-1-ehtyl-9-hydroxy-3-oxo-1,2,3,4-tetrahydrocyclopenta[c][1]benzopyran and 3-(1,2-dimethylheptyl-1-hydroxy-7-oxo-7,8,9,10-tetrahydro-6,6,10-trimethyl-6H-dibenzo[b,d]pyran.

The compounds of this invention have analgesic and tranquilizing activity in animals and such activities indicate potential human use for the compounds as drugs.

1-Acetoxy-6,6-dimethyl-3-(1,2-dimethylheptyl)-7-oxo-7,8,9,10-tetrahydro-6H-dibenzo[b,d]pyran when tested in mice for analgesic activity by the hot plate test [J. Pharmacol. Exper. Therap., 80, 300 (1944)] after oral administration was found to have an $ED_{50}$ of 38 mg/kg after 1 hour and an $ED_{50}$ of 20 mg/kg after 2 hours. By the rat rail flick test for analgesic activity [J. Pharmacol. Exper. Therap., 72, 74 (1941)] it increased the pain threshold of the rats by 39% at 5 mg/kg orally and 53% at 10 mg/kg orally. The tranquilizing activity of the compound was demonstrated in the rat motor activity test (Plotnikoff U.S. Pat. No. 3,755,584). At 5 mg/kg orally it increased motor activity 19%, at 20 mg/kg it decreased motor activity 2% and at 80 mg/kg it decreased motor activity 54%. The antagonism of this compound to methamphetamine-induced hyperactivity in rats when administered orally was also measured and found to give a 28% reduction in activity at 10 mg/kg orally; a 68% reduction at 20 mg/kg; and a 83% reduction at 80 mg/kg, thus further demonstrating its tranquilizing activity. The compound in mice (i.v.) showed a MED at 2.0 mg/kg for decrease in motor activity.

3-(1,2-dimethylheptyl)-1-hydroxy-7-oxo-7,8,9,10-tetrahydro-6,6,9-trimethyl-6H-dibenzo[b,d]pyran had an $ED_{50}$ in the hot plate test of 9.0 mg/kg orally, thus establishing that it has analgesic activity.

9-Acetoxy-4,4-dimethyl-7-(1,2-dimethylheptyl)-3-oxo-1,2,3,4-tetrahydrocyclopenta[c][1]benzopyran was found to have an MED in mice (i.v.) of 5.0 mg/kg for decrease in motor activity, thus indicating a potential tranquilizing activity.

The present invention includes within its scope pharmaceutical compositions comprising, as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration and on the duration of the treatment. Generally, dosage levels of between 0.1 to 40 mg/kg of body weight daily are administered to patients in need of analgesia or tranquilization.

The following is an illustration of the pharmaceutical compositions which are a feature of this invention:

TABLET COMPOSITION

Tablets weighing 100 mg. and having the following compositions are prepared by standard tableting procedures:

| Ingredient | Mg. |
|---|---|
| 1-Acetoxy-6,6-dimethyl-3-(1,2-dimethylheptyl)-7-oxo-7,8,9,10-tetrahydro-6H-dibenzo[b,d]pyran | 25 |
| Starch | 69 |
| Colloidal silica | 5 |
| Magnesium stearate | 1 |

The following examples are presented to further illustrate the invention.

EXAMPLE 1

1-Acetoyx-3-(1,2-dimethylheptyl)-7,8,9,10-tetrahydro-6,6,9-trimethyl-6H-dibenzo[b,d]pyran A solution of 3-(1,2-dimethylheptyl)-1-hydroxy-6,6,9-trimethyl-7,8,9,10-tetrahydro-6H-dibenzo[b,d]pyran (5.04 g., 16.6 mmole) and acetic anhydride (1.74 g., 17 mmole) in 20 ml. of pyridine was warmed over a steam bath with stirring for 2 hours. The reaction mixture was allowed to cool to room temperature and the pyridine was removed by evaporation under reduced pressure. To the residue was added 20 ml. of water and the aqueous mixture was extracted with three portions of ether. The ether extracts were washed several times with water, 6N HCl, again with water and dried over $NA_2$SO$_4$. Solvent evaporation under reduced pressure left 5.21 g. (93%) of an amber oil whose ir and nmr were in agreement with those of the proposed structure.

EXAMPLE 2

1-Acetoxy-3-(1,2-dimethylheptyl)-7-oxo-7,8,9,10-tetrahydro-6,6,9-trimethyl-6H-dibenzo[b,d]pyran To a stirring mixture of 1-acetoxy-3-(1,2-dimethylheptyl)-7,8,9,10-tetrahydro-6,6,9-trimethyl-6H-dibenzo[b,d]pyran (5.21 g., 12.6 mmole) in 35 ml. of 50% acetic acid and 10 ml. of chloroform under a nitrogen atmosphere, was added dropwise a solution of ceric ammonium nitrate (27.63 g., 50.4 mmole) in 70 ml. of 50% acetic acid. After the addition was complete, the reaction mixture was stirred over a steam bath. After 3 hours the mixture was poured onto ice with stirring. It was extracted into ether and the organic solvents were removed under reduced pressure. The residue was again taken up in ether, washed to neutrality with 5% NaHCO$_3$, washed with water and dried over Na$_2$SO$_4$. Evaporation of the solvents in vacuo left 8.34 g. (23%) of crude product whose tlc showed a blue fluorescent spot (silica gel, R$_f$0.66, 1:1 EtOAc/hexane).

Ir and nmr were in agreement with the assigned structure.

UV: $\lambda_{max}^{EtOH}$ 350 m$\mu$, $\epsilon$ 10,793; $\lambda$ 302 m$\mu$, $\epsilon$ 18,506; $\lambda$ 247 m$\mu$, $\epsilon$ 16,280; $\lambda$ 227 m$\mu$, $\epsilon$ 16,768; $\lambda$ 206 m$\mu$, $\epsilon$ 27,134.

EXAMPLE 3

3-(1,2-Dimethylheptyl)-1-hydroxy-7-oxo-7,8,9,10-tetrahydro-6,6,9-trimethyl-6H-dibenzo b,d]pyran H-dibenzo[

To 8.34 g. (0.02 mole) of 1-acetoxy-3-(1,2-dimethylheptyl)-7-oxo-7,8,9,10-tetrahydro-6,6,9-trimethyl-6H-dibenzo[b,d]pyran was added 10 ml. of 3.1 of M NaOH and the solution was stirred and warmed over a steam bath for 10 minutes. The reaction mixture was diluted with 10 ml. of water, cooled over ice, and acidified with concentrated HCl. It was then extracted with ether, washed several times with water, and dried over Na$_2$SO$_4$. The product obtained after evaporation of the solvent in vacuo was pre-chromatographed on magnesium silicate to remove colored impurities. A second chromatography on magnesium silicate (eluting with graded ether/petroleum ether) left 420 mg. of desired compound (tlc, silica gel, R$_f$0.33, 15% ether/petroleum ether). The ir and nmr of the compound were in agreement with the proposed structure.

UV: $\lambda_{max}^{EtOH}$ 335 m$\mu$, $\epsilon$ 15,726; $\lambda$ 249 m$\mu$, $\epsilon$ 5,128; $\lambda$ 228 m$\mu$, $\epsilon$ 14,530; $\lambda$ 211 m$\mu$, $\epsilon$ 25,470.

Anal. Calcd. for $C_{25}H_{36}O_3$: C, 78.1; H, 9.4. Found: C, 77,98; H, 9.38.

EXAMPLE 4

1-Acetoxy-6,6-dimethyl-3-(1,2-dimethylheptyl)-7,8,9,10-tetrahydro-6H-dibenzo[b,d]pyran A solution of 6,6-dimethyl-3-(1,2-dimethylheptyl)-1-hydroxy-7,8,9,10-tetrahydro-6H-dibenzo[b,d]pyran (9.3 g., 0.026 mole) and acetic anhydride (20.4 g., 0.2 mole) in 50 ml. of pyridine was warmed with stirring over a steam bath. After 2 hours the pyridine was removed by evaporation in vacuo. An ice water mixture was added to the residue. The product was extracted with ether and washed several times with water, 6N HCl, and water consecutively, and finally dried over Na$_2$SO$_4$. After removal of the solvent under reduced pressure, 10.3 g. (quantitative yield) of product was obtained, whose ir and nmr were indicative of the proposed acetate. On tlc (silica gel, 20% ether/petroleum ether), the product showed a spot at R$_f$ 0.75.

UV: $\lambda_{max}^{EtOH}$ 304 mμ, ε 4,219; λ 276 mμ, ε 5,648; λ 267 mμ, ε 7,641; λ258 mμ, ε 6,645; λ 223 mμ, ε 14,452; λ 204 mμ, ε 12,292.

EXAMPLE 5

1-Acetoxy-6,6-dimethyl-3-(1,2-dimethylheptyl)-7-oxo-7,8,9,10-tetrahydro-6H-dibenzo[b,d]pyran To a stirring mixture of 1-acetoxy-6,6-dimethyl-3-(1,2-dimethylheptyl)-7,8,9,10-tetrahydro-6H-dibenzo[b,d]pyran (10.3 g., 0.026 mole) in 90 ml. of 50% acetic acid and 25 ml. of chloroform under a nitrogen atmosphere, was added dropwise a solution of ceric ammonium nitrate (57.02 g., 0.104 mole) in 150 ml. of 50% acetic acid. After the addition was completed, the reaction mixture was stirred while heated over a steam bath for 1 hour. The reaction mixture was diluted with ice water and extracted into ether. The ethereal extract was separated and washed consecutively with water, 5% NaHCO$_3$, water, and finally dried over Na$_2$SO$_4$. Evaporation of the solvent under reduced pressure preceeded a pre-chromatography which separated out the inorganic material as well as some colored impurities. A second chromatography (magnesium silicate, eluting with graded ether/petroleum ether) yielded 1.0 g. (9.3%) of an amber material which gave a blue fluorescence on tlc (silica gel, R$_f$ 0.55, 1:1 ether/petroleum ether). Upon standing, the product solidified and was resolidified from ethanol/water to give a tan solid, m.p. 81°-83° C.

The ir and nmr spectra were in agreement with the proposed structure.

UV: $\lambda_{max}^{EtOH}$ 350 mμ, ε 9.365; λ 300 mμ, ε 15,556; λ 248 mμ, ε 13,598; λ 241 mμ, ε13,598; λ230 mμ, ε 13,281; λ 224 mμ, ε 13,333; λ 206 mμ, ε 23,862.

The 1-acetoxy group is readily hydrolyzed to give the corresponding 1-hydroxy compound using the procedure of Example 3.

EXAMPLE 6

1-Acetoxy-7,8,9,10-tetrahydro-3,6,6,9-tetramethyl-6H-dibenzo[b,d]pyran

A solution of 1-hydroxy-7,8,9,10-tetrahydro-3,6,6,9-tetramethyl-6H-dibenzo[b,d]pyran (9.07 g., 0.035 mole) and acetic anhydride (7.1 g., 0.07 mole) in 25 ml. of pyridine was warmed over a steam bath for 2 hours. The reaction mixture was allowed to cool to room temperature and pyridine was removed by evaporation under reduced pressure. Water was added to the residue and the aqueous mixture was extracted with three portions of ether. The ethereal extracts were combined, washed with water, 6N HCl, again with water, dried over Na$_2$SO$_4$ and concentrated under reduced pressure to 9.5 g. (90%) of a colorless solid, m.p. 115°-119° C.

The ir and nmr were consistent with the proposed structure.

EXAMPLE 7

1-Acetoxy-7-oxo-7,8,9,10-tetrahydro-3,6,6,9-tetramethyl-6H-dibenzo[b,d]pyran

To a stirring mixture of 1-acetoxy-7,8,9,10-tetrahydro-3,6,6,9-tetramethyl-6H-dibenzo[b,d]pyran (601 mg., 2 mmole) in 7 ml. of 50% acetic acid and 5 ml. of chloroform held under a nitrogen atmosphere, was added dropwise a solution of ceric ammonium nitrate (4.39 g., 8 mmole) in 12 ml. of 50% acetic acid. After the addition was completed, the reaction mixture was stirred over a steam bath. After 3 hours, the mixture was poured onto ice with stirring. The product was extracted into ether, washed to neutrality with 5% NaHCO$_3$, washed with water, dried over Na$_2$SO$_4$ and concentrated under reduced pressure. Elution of the product from a mganesium silicate column with graded ether/petroleum ether gave 120 mg. (14.2%) of the desired product which showed a blue fluorescent spot on tlc at R$_f$ 0.67 (silica gel, 40% EtOAc/hexane). Ir(neat) 1770(m), 1740(s), 1660(s), 1640(s), 1620(m) CM$^{-1}$; nmr (CDCl$_3$) δ 1.08(d,3H, J=4Hz), 1.38(S,3H), 1.7(S,3H), 2.3(S,6H), 1.0–3.0(broad m,5H), 6.5(S,1H), 6.62(S,1H).

Anal. Calcd. for C$_{19}$H$_{22}$O$_4$: C, 72.59; H, 7.06. Found: C, 72.53; H, 7.12.

The 1-acetoxy compound so produced is readily converted by hydrolysis to the otherwise corresponding 1-hydroxy compound following the procedure of Example 3.

EXAMPLE 8

9-Acetoxy-4,4-dimethyl-7-(1,2-dimethylheptyl)-1,2,3,4-tetrahydrocyclopenta[c][l]benzopyran A solution of 4,4-dimethyl-9-hydroxy-7-(1,2-dimethylheptyl)-1,2,3,4-tetrahydrocyclopenta[c][l]benzopyran (6.85 g., 0.02 mole) and acetic anhydride (3.06 g., 0.03 mole) in 20 ml. of pyridine was warmed over a steam bath with stirring for 2 hours. The reaction mixture was allowed to cool to room temperature and the pyridine was removed by evaporation under reduced pressure. Water was added to the residue and this aqueous mixture was extracted with three portions of ether. The ether extracts were washed several times with water, 6N HCl, again with water, and dried over Na$_2$SO$_4$. Solvent evaporation in vacuo left 7.59 g. (99%) of crude acetate. The ir and nmr were in agreement with the proposed structure.

EXAMPLE 9

9-Acetoxy-4,4-dimethyl-7-(1,2-dimethylheptyl)-3-oxo-1,2,3,4-tetrahydrocyclopenta[c][l]benzopyran To a stirring mixture of 9-acetoxy-4,4-dimethyl-7-(1,2-dimethylheptyl)-1,2,3,4-tetrahydrocyclopenta[c][l]benzopyran (7.59 g., 19.7 mmole) in 60 ml. of 50% acetic acid and 10 ml. of chloroform under a nitrogen atmosphere, was added dropwise a solution of ceric ammonium nitrate (43.2 g., 78.8 mmole) in 100 ml. of 50% acetic acid. After the addition was completed, the reaction mixture was stirred over a steam bath for ½ hour. It was then extracted with several portions of chloroform and the organic solvents were removed by evaporation under reduced pressure. The residue was taken up in ether, neutralized with 5% NaHCO$_3$, washed with water and dried over Na$_2$SO$_4$. Evaporation of the ether in vacuo left 14.7 g. of crude material. Purification of the crude product involved three chromatograhpies, two column and a final preparative thin-layer chromatography, with each using diethyl ether/petroleum ether solvent mixtures. An nmr spectrum taken at this time, however, showed that the compound had been partially deacetylated as a result of the chromatograhpies. The product was reacetylated in the usual manner by heating the pyran with acetic anhydride in pyridine. Upon workup, 57 mg. of product was obtained which gave a single fluorescent spot on tlc (R$_f$ 0.41). The ir and nmr were in agreement with the proposed structure.

The 9-acetoxy compound is readily hydrolyzed according to Example 3 to yield the corresponding 9-hydroxy compound.

EXAMPLE 10

3-(4-p-Fluorophenyl-1-methylbutyl)-1-hydroxy-7-oxo-7,8,9,10-tetrahydro-6,6,9-trimethyl-6H-dibenzo[b,d]pyran 3-(4-p-fluorophenyl-1-methylbutyl)-1-hydroxy-7,8,9,10-tetrahydro-6,6,9-trimethyl-6H-dibenzo[b,d]pyran, prepared as disclosed in Winn et al. U.S. Pat. No. 3,901,926, is converted to the 1-acetoxy compound according to the procedure of Example 1, the 1-acetoxy compound is converted to 1-acetoxy-3-(4-p-fluorophenyl-1-methylbutyl)-7-oxo-7,8,9,10-tetrahydro-6,6,9-trimethyl-6H-dibenzo[b,d]pyran according to Example 2 and this compound upon hydrolysis according to Example 3 gives 3-(4-p-fluorophenyl-1-methylbutyl)-1-hydroxy-7-oxo-7,8,9,10-tetrahydro-6,6,9-trimethyl-6H-dibenzo[b,d]pyran.

EXAMPLE 11

4,4-Dimethyl-7-(5-p-fluorophenylpentyl)-9-hydroxy-3-oxo-1,2,3,4-tetrahydro-cyclopenta[c][1]benzopyran 4,4-Dimethyl-7-(5-p-fluorophenylpentyl)-9-hydroxy-1,2,3,4-tetrahydrocyclopenta[c][1]benzopyran, prepared according to Winn et al. U.S. Pat. No. 3,901,926, is converted to the 9-acetoxy compound according to Example 8 and then the 9-acetoxy compound is oxidized according to Example 9 to produce 9-acetoxy-4,4-dimethyl-7-(5-p-fluorophenylpentyl)-3-oxo-1,2,3,4-tetrahydrocyclopenta[c][1]benzopyran which upon hydrolysis according to Example 3 yields 4,4-dimethyl-7-(5-p-fluorophenylpentyl)-9-hydroxy-3-oxo-1,2,3,4-tetrahydro-cyclopenta[c][1]benzopyran.

The foregoing detailed description has been given for clearness of understanding only, and no unnecessary limitations should be understood therefrom, as modifications will be obvious to those skilled in the art.

What is claimed is:

1. A compound of the formula

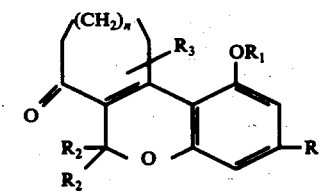

wherein n represents 0 or 1, R is an alkyl group having 1 to 20 carbon atoms, an aryl-lower group or a cycloalkyl-lower alkyl group, R$_1$ is hydrogen or

wherein R$_4$ is lower alkyl, phenyl, cycloalkyl-lower or aryl-lower alkyl, R$_2$ is a lower alkyl and R$_3$ is hydrogen or one or two lower alkyl groups.

2. A compound according to claim 1 in which R$_4$ is a lower alkyl group, R$_2$ is methyl and R$_3$ is hydrogen or one or two methyl groups.

3. A compound according to claim 1 in which R$_1$ is hydrogen, R$_2$ is methyl and R$_3$ is hydrogen or one or two methyl groups.

4. A compound according to claim 1 named 1-acetoxy-3-(1,2-dimethylheptyl)-7-oxo-7,8,9,10-tetrahydro-6,6,9-trimethyl-6H-dibenzo[b,d]pyran.

5. A compound according to claim 1 named 1-acetoxy-6,6-dimethyl-3-(1,2-dimethylheptyl)-7-oxo-7,8,9,10-tetrahydro-6H-dibenzo[b,d]pyran.

6. A compound according to claim 1 named 1-acetoxy-7-oxo-7,8,9,10-tetrahydro-3,6,6,9-tetramethyl-6H-dibenzo[b,d]pyran.

7. A compound according to claim 1 named 9-acetoxy-4,4-dimethyl-7-(1,2-dimethylheptyl)-3-oxo-1,2,3,4-tetrahydrocyclopenta[c][1]benzopyran.

8. A compound according to claim 1 named 4,4-dimethyl-7-(1,2-dimethylheptyl)-9-hydroxy-3-oxo-1,2,3,4-tetrahydrocyclopenta[c][1]benzopyran.

9. A compound according to claim 1 named 3-(4-p-fluorophenyl-1-methylbutyl)-1-hydroxy-7-oxo-7,8,9,10-tetrahydro-6,6,9-trimethyl-6H-dibenzo[b,d]pyran.

10. A compound according to claim 1 named 4,4-dimethyl-7-(5-p-fluorophenylpentyl)-9-hydroxy-3-oxo-1,2,3,4-tetrahydrocyclopenta[c][1]benzopyran.

11. A compound of the formula

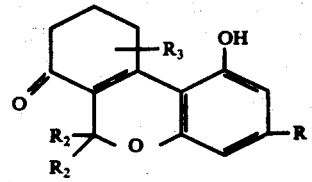

wherein R is an alkyl group having 1 to 20 carbon atoms, an aryl-lower alkyl group or a cycloalkyl-lower alkyl group, R$_2$ is a lower alkyl and R$_3$ is hydrogen or one or two lower alkyl groups.

12. A compound according to claim 11 in which R$_2$ is methyl and R$_3$ is hydrogen or one or two methyl groups.

13. A compound according to claim 11 named 3-(1,2-dimethylheptyl)-1-hydroxy-7-oxo-7,8,9,10-tetrahydro-6,6,9-trimethyl-6H-dibenzo[b,d]pyran.

14. A compound according to claim 11 named 6,6-dimethyl-3-(1,2-dimethylheptyl)-1-hydroxy-7-oxo-7,8,9,10-tetrahydro-6H-dibenzo[b,d]pyran.

15. A compound according to claim 11 named 1-hydroxy-7-oxo-7,8,9,10-tetrahydro-3,6,6,9-tetramethyl-6H-dibenzo[b,d]pyran.

* * * * *

UNITED STATES PATENT AND TRADEMARK OFFICE
CERTIFICATE OF CORRECTION

PATENT NO. : 4,051,152
DATED : September 27, 1977
INVENTOR(S) : Razdan et al.

It is certified that error appears in the above-identified patent and that said Letters Patent are hereby corrected as shown below:

Column 2, line 38, in the formula change "4↘₈" to --⁰↘₈--; column 3, line 62, place an arrow (⟶) before formula VII; column 4, line 7, change "hydroxyl-" to --hydroxy- line 42, before "basic" insert --a--; column 5, line 1, change "pentac]" to --penta[c]--; column 6, line 13, change "ehtyl" to --ethyl--, line 26, change "rail" to --tail--, line 65, place a comma (,) after "practice"; column 7, line 41, change "compositions" to --composition--, last line, change "NA$_2$" to --Na$_2$--; column 8, line 33, change "b,d]" to --[b,d]--, line 34, delete "H-dibenzo["; line 44, change "So$_4$" to --SO$_4$--; column 10, line 11, change "mganesium" to --magnesium--, line 15, change "CM$^{-1}$" to --Cm$^{-1}$--, lines 63 and 68, change "chromatograhpies" to --chromatographies--; column 12, line 6, after "lower" insert --alkyl--.

Signed and Sealed this

Seventh Day of March 1978

[SEAL]

Attest:

RUTH C. MASON
Attesting Officer

LUTRELLE F. PARKER
Acting Commissioner of Patents and Trademarks